United States Patent [19]
Rock et al.

[11] Patent Number: 6,002,053
[45] Date of Patent: Dec. 14, 1999

[54] PROCESS FOR PREPARING PENTAFLUOROPENTANOL

[75] Inventors: Michael-Harold Rock, Valby, Denmark; Albrecht Marhold, Leverkusen, Germany

[73] Assignee: Bayer Aktiengesellschaft, Leverkusen, Germany

[21] Appl. No.: 09/156,988

[22] Filed: Sep. 18, 1998

[30] Foreign Application Priority Data

Oct. 14, 1997 [DE] Germany ............................ 197 45 374
Nov. 5, 1997 [DE] Germany ............................ 197 48 775

[51] Int. Cl.[6] .................................................. C07C 31/34
[52] U.S. Cl. .............................................................. 568/842
[58] Field of Search .............................................. 568/842

[56] References Cited

U.S. PATENT DOCUMENTS

| | | | |
|---|---|---|---|
| 3,145,222 | 8/1964 | Brace | 260/408 |
| 4,073,817 | 2/1978 | Jager | 260/653.1 |
| 5,254,754 | 10/1993 | Amimoto | 568/842 |
| 5,502,046 | 3/1996 | Bohlmann et al. | |

FOREIGN PATENT DOCUMENTS

| | | |
|---|---|---|
| 0623140 B1 | 4/1998 | European Pat. Off. . |
| 4132182 A1 | 3/1993 | Germany . |
| WO93/13123 | 7/1993 | WIPO . |

OTHER PUBLICATIONS

Kitazume, T and N Ishikawa. "Ultrasound–Promoted Selective Perfluoroalkylation on the Desired Position of Organic Molecules" *J. Am. Chem. Soc.* (1985) vol. 107, No. 18, pp. 5186–5191, published in US.

Larsson, U. "Synthesis of Amino Acids with Modified Principal Properties 1. Amino Acids with Fluorinated Side Chains" *Acta Chemica Scandinavia* (1993), vol. 47, pp. 380–390, published in Belgium.

Li, X et al., "Laboratory Scale Preparation of 4,4,5,5,5–Pentafluoropentan–1–thiol: An Important Chain of Anti–Breast Cancer Agents" *Tetrahedron Letters* (1994) vol. 35, No. 49, pp. 9141–9144, published in UK.

Park, JD et al. "Free–Radical Catalyzed Addition of Unsaturated Alcohols to Perhaloalkanes" *J. Org. Chem.* (Jun. 1961) vol. 26, pp. 2089–2095, published in US.

*Primary Examiner*—Michael L. Shippen
*Attorney, Agent, or Firm*—Brinks Hofer Gilson & Lione

[57] ABSTRACT

4,4,5,5,5-Pentafluoro-1-pentanol is prepared in a particularly advantageous manner from perfluoroethyl iodide by initially adding perfluoroethyl iodide in the presence of a radical initiator which does not carry any acyl groups to allyl alcohol and then hydrogenolytically dehalogenating the resulting 4,4,5,5,5-pentafluoro-2-iodo-1-pentanol in the presence of a catalyst, an acid binder and a diluent.

11 Claims, No Drawings

PROCESS FOR PREPARING PENTAFLUOROPENTANOL

The present invention relates to an improved process for preparing 4,4,5,5,5-pentafluoro-1-pentanol from perfluoroethyl iodide.

4,4,5,5,5-Pentafluoro-1-pentanol is a useful intermediate for the preparation of pharmaceutics (see, for example, DE-A 41 32 182 and Tetrahedron Lett. 35, 9141 (1994)).

Three processes for preparing 4,4,5,5,5-pentafluoro-1-pentanot are disclosed in the literature.

Two of these processes employ perfluoroethyl iodide and propargyl alcohol as starting materials. In the first process (Tetrahedron Lett., loc. cit.), the sodium dithionite/sodium bicarbonate-initiated free-radical addition affords 4,4,5,5,5-pentafluoro-2-iodo-2-penten-1-ol in good yield. In the second step, again in good yield, this is then simultaneously catalytically hydrogenated and dehalogenated with hydrogen in the presence of two equivalents of triethylamine and platinum oxide. However, the decisive disadvantage of this process is the amount of expensive platinum oxide that is required (2.5 g for less than 30 g of product).

In the second process (DE-A 41 32 182 and WO 93/13123), the ultrasound-promoted addition is carried out via perfluoroalkyl cuprate, which is formed in the presence of zinc and copper (I) iodide, to give 4,4,5,5,5-pentafluoro-2-penten-1-ol, as described in J. Am. Chem. Soc. 107, 5186 (1985). This is followed by catalytic hydrogenation using platinum oxide (DE-A 41 32 182) or Raney nickel (WO 93/13123) as catalyst. 5% of the amount of catalyst of the abovementioned dehalogenating hydrogenation is sufficient here, but the poor yield in the first reaction step of only 46% of theory and the technically complicated use of ultrasound are disadvantageous.

Furthermore, the potential risk of acetylene formation in the propargyl alcohol, in particular at the high temperatures which occur locally during irradiation with ultrasound, has to be considered in the two processes.

The third process entails three steps and also uses perfluoroethyl iodide as starting material (Acta Chem. Scand. 47, 380 (1993)). A free-radical addition initiated by 2,2-azo-bis-isobutyronitrile (AIBN) to allyl acetate gives 5-acetoxy-4-iodo-1,1,1,2,2-pentafluoropentane, which is dehalogenated in a free-radical reaction using tributyltin hydride. The resulting 5-acetoxy-1,1,1,2,2-pentafluoropentane is hydrolyzed in the final step using alkali. The disadvantages of this process are the high number of reaction steps and the reaction with tributyltin hydride, which is difficult to control and thus virtually impossible to carry out on a larger scale.

Finally, it is also known that pentafluoroethyl iodide can be reacted with allyl alcohol in the presence of benzyl peroxide. (J. Org. Chem. 26, 2089 (1981)). However, the yield, even after a reaction time of 14 days, is only 55% of theory.

The only 4,4,5,5,5-pentafluoro-1-pentanol which is commercially available has a purity of approximately 95%. Such a purity is insufficient for the preparation of active compounds.

This invention, accordingly, provides a process for preparing 4,4,5,5,5-pentafluoro-1-pentanol from perfluoroethyl iodide, which comprises initially adding perfluoroethyl iodide in the presence of a radical initiator which does not carry any acyl groups to allyl alcohol and then hydrogenolytically dehalogenating the resulting 4,4,5,5,5-pentafluoro-2-iodo-1-pentanol in the presence of a catalyst, an acid binder and a diluent.

The chemicals perfluoroethyl iodide and allyl alcohol which are required as starting materials for the process according to the invention are commercially available.

Radical initiators which do not carry acyl groups are, for example, dithionite/bicarbonate mixtures, di-tert-butyl peroxide, 2,2-azo-bis-isobutyronitrile (AIBN) or light, for example of a high-pressure mercury arc lamp or a tungsten filament lamp. Suitable radical initiators which do not carry any acyl groups are also complex metal compounds, for example those which contain one or more central atoms from the group of the transition metals, in particular from the group consisting of iron, cobalt and nickel, and which contain dienyl and/or carbonyl ligands. Preference is given to the system sodium dithionite/sodium bicarbonate and to the dimeric metal compound cyclopentadienyliron dicarbonyl $[Cp(CO)_2Fe]_2$.

Dithionite/bicarbonate mixtures may contain, for example, 0.5 to 2 mol of bicarbonate per mole of dithionite. This ratio is preferably 1:0.7 to 1.5. It is possible to use, for example, such an amount of dithionite/bicarbonate mixture or complex metal compounds that 1 to 5 mol, preferably 1.1 to 3 mol, of dithionite are employed per mole of perfluoroethyl iodide.

Organic radical initiators which do not carry any acyl groups can also be employed in smaller amounts, for example of from 0.01 to 0.5 mol, in particular 0.05 to 0.2 mol, per mole of perfluoroethyl iodide.

The addition can be carried out in the presence or the absence of a diluent. When using dithionite/bicarbonate mixtures, it is advantageous to employ water or mixtures of water-soluble organic solvents with water (water content preferably at least 30% by volume). When using organic radical initiators which do not carry any acyl groups, light or complex metal compounds, it is preferable to employ organic solvents, for example organic solvents which are immiscible or miscible with water, or to carry out the reaction without a diluent. Suitable water-miscible solvents are, for example: nitriles, such as acetonitrile, propionitrile, n- and i-butyronitrile, and alcohols, such as methanol, ethanol, n- and i-propanol, n-, i-, s- and t-butanol, ethanediol, propane-1,2-diol, ethoxyethanol, methoxyethanol, diethylene glycol monomethyl ester and diethylene glycol monoethyl ester. Preference is given to acetonitrile/water mixtures. It is possible to employ, for example, 50 ml to 3 l of diluent per mole of pentafluoroethyl iodide.

The temperature for the addition can be varied within a wide range. When dithionite/bicarbonate mixtures are used, preference is given to carrying out the reaction at −50 to +25° C., particularly preferably at −20 to +25° C. The reaction is generally carried out under atmospheric pressure. However, it is also possible to carry out the reaction under reduced or elevated pressure. When other radical initiators are used, it is possible to select other temperatures, if appropriate. However, in each case it has to be ensured that sufficient radicals are formed from the radical initiator.

It is possible to employ pentafluoroethyl iodide and allyl alcohol in molar ratios of from 1:0.7 to 20, for example. This ratio is preferably 1:0.9 to 2.

After the addition has ended, the reaction mixture can be worked up, for example, by extraction with a suitable solvent. Solvents which are suitable for this purpose are, for example, ethyl acetate and methyl tert-butyl ether. It is also possible to add water to the reaction mixture and to remove volatile components under reduced pressure.

Suitable catalysts used for the second reaction step, the hydrogenolytic dehalogenation, are, for example, heterogeneous hydrogenation catalysts such as platinum oxide, palladium on carbon or Raney nickel. Preference is given to using palladium on carbon having a palladium content of 2 to 10% by weight. The amount of catalyst can be varied within wide limits. It is possible to use, for example, 0.001 to 1% by weight, preferably 0.01 to 0.1% by weight, of catalyst (calculated as metal), based on 4,4,5,5,5-pentafluoro-2-iodo-1-pentanol.

Suitable acid binders for the hydrogenolytic dehalogenation are, for example, inorganic and organic bases. Examples which may be mentioned are: bicarbonates such as sodium bicarbonate and potassium bicarbonate, primary, secondary and tertiary amines such as methylamine, dimethylamine, ethylamine, diethylamine, trimethylamine, triethylamine, tributylamine, N,N-dimethylaniline, N,N-dimethylbenzylamine, pyridine, N-methylpyridine, N-methylmorpholine, N,N-dimethylaminopyridine, diazabicyclooctane (DABCO), diazabicyclononene (DBN) and diazabicycloundecene (DBU) and alkanolamines such as methylolamine, dimethylolamine, trimethylolamine, ethanolamine, diethanolamine, triethanolamine and the corresponding $C_3$–$C_6$-alkanolamines. Preference is given to using triethylamine or monoalkanolamine.

Suitable diluents for carrying out the hydrogenolytic dehalogenation according to the invention are, for example, water, organic solvents and any mixtures thereof. Suitable organic solvents are, for example: aliphatic and alicyclic hydrocarbons, such as petroleum ether, hexane, heptane, cyclohexane and methylcyclohexane, ethers, such as diethyl ether, diisopropyl ether, methyl-t-butyl ether and methyl t-amyl ether, dioxane, tetrahydrofuran, 1,2-dimethoxyethane, 1,2-diethoxyethane, diethylene glycol dimethyl ether and anisole, esters, such as methyl acetate, ethyl acetate and butyl acetate, and alcohols, such as methanol, ethanol, n- and i-propanol, n-, i-, s- and t-butanol, ethanediol, propane-1,2-diol, ethoxyethanol, methoxyethanol, diethylene glycol monomethyl ether and diethylene glycol monoethyl ether. Preference is given to methyl-t-butyl ether and ethyl acetate and to the combination of water with alkanolamines as acid binders.

The reaction temperature for the hydrogenolytic dehalogenation can be varied within a wide range. The reaction can be carried out, for example, at −20 to +100° C., preferably at 0 to 50° C. The hydrogen pressure can be, for example, 5 to 300 bar, preferably 20 to 100 bar. When particularly active catalysts are used, it is also possible to operate in the pressure range of 1 to 5 bar. During the reaction, the desired hydrogen pressure has to be maintained, if appropriate, by subsequent addition.

It is possible to use, for example 0.9 to 2 equivalents, preferably 1 to 1.5 equivalents of acid binder and 100 to 1000 ml of diluent per mole of 4,4,5,5,5-pentafluoro-2iodo-1-pentanol.

It is an essential feature of the process according to the invention that the 4,4,5,5,5-pentafluoro-2-iodo-1-pentanol is hydrogenated in the presence of a diluent, a catalyst and an acid binder. For example, it is possible to initially charge the catalyst, acid binder and diluent under an atmosphere of hydrogen and to meter in 4,4,5,5,5-pentafluoro-2-iodo-1-pentanol and, if appropriate, hydrogen at the rate of its consumption to maintain the pressure. It is also possible to initially charge the starting material, catalyst, diluent and acid binder and then to carry out hydrogenation by application of hydrogen pressure. 4,4,5,5,5-Pentafluoro-1-pentanol can be obtained in high yields.

Work-up can be carried out, for example, by adding water to dissolve the iodide salt which has been formed, followed by extraction of the product, if appropriate after removal of the hydrogenation catalyst by filtration. If appropriate, the solution of the crude product can be subjected to fractional distillation for further purification.

The process according to the invention has a number of surprising advantages. Thus, hydrogenation catalysts are required in customary amounts and not in disproportionately high amounts, the desired product is obtained in high yields in a technically simple manner, the handling of chemicals which, owing to their risk potential, require particular expenditure is not required, the use of ultrasound is avoided, and the process can be carried out without any problems even on a relatively large scale. It is particularly surprising that the addition, according to the invention, of pentafluoroethyl iodide to allyl alcohol succeeds in yields of more than 75%. Additionally, the 4,4,5,5,5-pentafluoro-1-pentanol can be obtained in higher purities of up to 99.9%, suitable for further processing to give active compounds. 4,4,5,5,5pentafluoro-1-pentanol is thus considerably more accessible than before.

EXAMPLES

Example 1

Preparation of 4,4,5,5,5-pentafluoro-2-iodo-1-pentanol

With stirring and at −10 to −5° C., 440 g of pentafluoroethyl iodide were added to a solution of 105 g of allyl alcohol, 1800 ml of acetonitrile and 1400 ml of water. A mixture of 335 g of 95% strength by weight sodium dithionite and 170 g of sodium bicarbonate was then added all at once, and the reaction mixture was kept at a temperature of below 0° C. with stirring. After 60 minutes, the reaction mixture was allowed to warm slowly to room temperature. The resulting suspension was poured into 2000 ml of water and extracted twice with 750 ml of ethyl acetate each time. The combined organic phases were dried and concentrated, giving 430 g (=80% of theory) of 4,4,5,5,5-pentafluoro-2-iodo-1-pentanol in the form of a brown oil. According to GC, the product was 99% pure, and it was used without any further purification for Example 3.

Example 2

By the method of Example 1, 130 g of perfluoroethyl iodide were reacted with 300 g of allyl alcohol in 380 ml of water, initiated by 100 g of sodium dithionite and 50 g of sodium bicarbonate. This gave 97 g (=61% of theory) of 4,4,5,5,5-pentafluoro-2-iodo-1-pentanol of a purity of 97% (GC).

Example 3

200 ml of methanol were mixed with 240 g of allyl alcohol, cooled to 0 to 5° C. and initially charged, and 1000 g of pentafluoroethyl iodide were added. 18.0 g of dimeric cyclopentadienyliron dicarbonyl were subsequently added. The reaction mixture was warmed to room temperature and stirred for 12 hours at 23 to 26° C. A reflux condenser which was operated at −5° C. prevented the evaporation of pentafluoroethyl iodide. For work-up 80 g of water were added to the reaction mixture and the easily volatile components were then removed at 5 mbar. 1120 g of 4,4,5,5,5-pentafluoro-2-iodo-1-pentanol remained. Purity 95% (CC).

Example 4

Preparation of 4,4,5,5,5-pentafluoro-1-pentanol

In a stirred autoclave with a capacity of 40 l, 15 l of ethyl acetate, 4.5 l of triethylamine and 100 g of palladium on carbon (5% by weight of palladium) were initially charged, and a hydrogen pressure of 60 bar was applied. Over the course of 24 hours, 8.5 kg of 4,4,5,5,5-pentafluoro-2-iodo-1-pentanol (obtained by the procedure of Example 1) were metered in, and the hydrogen pressure was maintained at 40 to 60 bar during this time. After the addition had ended, stirring was continued for another 2 hours. According to GC analysis, the reaction was then complete. The autoclave was vented, 10 l of water were added to the reaction mixture and the catalyst was separated off by filtration. The filtrate was extracted with ethyl acetate and the combined organic phases were dried. Part of the solvent was initially evaporated by reducing the pressure to 120 mbar. The mixture that remained was distilled under reduced pressure. This gave 4400 g (=88% of theory) of 4,4,5,5,5-pentafluoro-1-pentanol of a purity of 97% (GC). The boiling point of the product was 134–135° C. at atmospheric pressure.

Example 5

By the method of Example 3, 1000 ml of methyl tert-butyl ether, 270 ml of triethylamine and 10.0 g of palladium on carbon were initially charged, and 500 g of 4,4,5,5,5-pentafluoro-2-iodo-1-pentanol were dehalogenated using hydrogen. This gave 217 g (=75% of theory) of 4,4,5,5,5-pentafluoro-1-pentanol of a purity of 98% (GC).

Example 6

A mixture of 180 ml of ethanolamine, 820 ml of water and 12 g of palladium on carbon (5% by weight of palladium) was initially charged, and a hydrogen pressure of 60 bar was applied. Over the course of 12 hours, 600 g of 4,4,5,5,5-pentafluoro-2-iodo-1-pentanol (obtained by the procedure of Example 1) were metered in. The temperature was kept at 30° C. and the hydrogen pressure was kept at 50 to 60 bar. After the metering in had ended, the reaction mixture was stirred for another 2 hours and the completion of the conversion was monitored by gas chromatography. Under reduced pressure, 4,4,5,5,5-pentafluoro-1-pentanol, together with water, was distilled off from the reaction mixture. Two phases formed in the distillate. The organic phase was separated off, the aqueous phase was extracted with dichloromethane and the extract was combined with the organic phase. The combined phases were dried, the solvent was distilled off and the product was purified by distillation. This gave 237 g (=88% of theory) of 4,4,5,5,5-pentafluoro-1-pentanol having a boiling point of 130° C. at 1013 mbar. Purity 99.9% (GC).

We claim:

1. A process for preparing 4,4,5,5,5-pentafluoro-1-pentanol from perfluoroethyl iodide, which comprises initially adding perfluoroethyl iodide in the presence of a radical initiator which does not carry any acyl groups to allyl alcohol and then hydrogenolytically dehalogenating the resulting 4,4,5,5,5-pentafluoro-2-iodo-1-pentanol in the presence of a catalyst, an acid binder and a diluent.

2. The process as claimed in claim 1, wherein the radical initiator used is a dithionite/bicarbonate mixture, di-tert-butyl peroxide, 2,2-azo-bis-isobutyronitrile (AIBN), light or a complex metal compound.

3. The process as claimed in claim 1, wherein dithionite/bicarbonate mixtures are employed which contain 0.5 to 2 mol of bicarbonate per mole of dithionite, and such an amount of dithionite/bicarbonate mixture is used that 1 to 5 mol of dithionite are employed per mole of perfluoroethyl iodide.

4. The process as claimed in claim 1, wherein the radical initiator used is a complex metal compound in an amount of from 1 to 5 mol per mole of perfluoroethyl iodide.

5. The process as claimed in claim 1, wherein organic radical initiators which do not carry any acyl groups are employed in amounts of from 0.01 to 0.5 mol per mole of pentafluoroethyl iodide.

6. The process as claimed in claim 1, wherein the addition is carried out in the presence of a diluent.

7. The process as claimed in claim 1, wherein the addition is carried out using sodium dithionite/sodium bicarbonate mixtures at −50 to +20° C.

8. The process as claimed in claim 1, wherein pentafluoroethyl iodide and alkyl alcohol are employed in molar ratios of from 1:0.7 to 20.

9. The process as claimed in claim 1, wherein the catalyst used is platinum oxide, palladium on carbon or Raney nickel.

10. The process as claimed in claim 1, wherein the acid binder used is a hydrogen carbonate, a primary, secondary or tertiary amine or an alkanolamine, and the reaction is carried out at −20 to +100° C.

11. The process as claimed in claim 1, wherein 0.9 to 2 equivalents of acid binder and 100 to 1000 ml of diluent are employed per mole of 4,4,5,5,5-pentafluoro-2-iodo-1-pentanol.

* * * * *